US005899877A

United States Patent [19]

Leibitzki et al.

[11] Patent Number: 5,899,877

[45] Date of Patent: May 4, 1999

[54] ONE-PIECE DISPENSING DEVICE FOR THE CONTAMINATION-FREE ADMINISTRATION OF MEDICAMENTS (CYTOSTATICA)

[75] Inventors: Harry Leibitzki, Halberstadt; Marina Menz, Jena; Norbert Neubauer, Halberstadt; Sebastian Vogt, Jena; Gerhard Wienzek, Halberstadt, all of Germany

[73] Assignee: Primed Halberstadt Medizintechnik GmbH, Halberstadt, Germany

[21] Appl. No.: 08/732,480

[22] PCT Filed: Apr. 25, 1995

[86] PCT No.: PCT/EP95/01547

§ 371 Date: Oct. 15, 1996

§ 102(e) Date: Oct. 15, 1996

[87] PCT Pub. No.: WO95/29661

PCT Pub. Date: Nov. 9, 1995

[30] Foreign Application Priority Data

| | | | |
|---|---|---|---|
| Apr. 28, 1994 | [DE] | Germany | 94 07 022 U |
| Jun. 29, 1994 | [DE] | Germany | 44 22 960 |
| Sep. 21, 1994 | [DE] | Germany | 44 33 669 |

[51] Int. Cl.[6] .... A61M 37/00

[52] U.S. Cl. .... 604/23

[58] Field of Search .... 604/80–81, 23, 604/49, 53, 82–85, 30–34, 131, 151, 246, 247

[56] References Cited

U.S. PATENT DOCUMENTS

| | | | |
|---|---|---|---|
| 4,114,617 | 9/1978 | Turner et al. | 604/80 |
| 4,200,095 | 4/1980 | Reti | 604/81 |
| 4,675,020 | 6/1987 | McPhee . | |
| 4,705,505 | 11/1987 | Fried | 604/80 |
| 4,863,454 | 9/1989 | LaBove . | |
| 4,973,328 | 11/1990 | Smith . | |
| 5,242,392 | 9/1993 | Vaughn . | |

FOREIGN PATENT DOCUMENTS

| | | |
|---|---|---|
| 0028198 | 5/1981 | European Pat. Off. . |
| 0273015 | 6/1988 | European Pat. Off. . |
| 0327519 | 8/1989 | European Pat. Off. . |
| 0330130 | 8/1989 | European Pat. Off. . |
| 0363770 | 4/1990 | European Pat. Off. . |
| 0416454 | 3/1991 | European Pat. Off. . |
| 0548577 | 6/1993 | European Pat. Off. . |

*Primary Examiner*—John D. Yasko
*Assistant Examiner*—Manuel Mendez
*Attorney, Agent, or Firm*—Jordan and Hamburg LLP

[57] ABSTRACT

A one-piece dispensing device for the contamination-free administration of medicaments (cytostatica) is particularly suitable for use in ambulant treatment. The invention provides a connector for connecting medicament (cytostatica) containers to instruments by which the medicaments are administered. The connector is designed to prevent, without a complex apparatus, contamination of the surroundings during connection of the container and until its disposal. The dispensing device has at least one coupling member to create a non-releasable connection with a medicaments container. The coupling member has an insertion pin and barbed surfaces to accommodate the medicaments container. The coupling member is non-releasably connected via a tube to a flexible container which is to be filled with gas. The flexible container is non-releasably connected to a further tube outlet and a mechanically actuated stop valve is incorporated in each of the connecting tubes.

12 Claims, 2 Drawing Sheets

ONE-PIECE DISPENSING DEVICE FOR THE CONTAMINATION-FREE ADMINISTRATION OF MEDICAMENTS (CYTOSTATICA)

BACKGROUND OF THE INVENTION

The invention relates to a one-piece dispensing device for contamination-free administration of medicaments (cytostatica), particularly for use in ambulant treatment.

For mixing and transferring pharmaceutical solutions from one container to at least another one it is required to embody the connection in such a manner that an escape of pharmaceutic agents and, thus, a contamination of the container surface and of the health care workers is eliminated. In particular, with respect to the mixing and administration of highly toxic cytostatic solutions, which can cause diseases when escaping uncontrolled, a contamination-free transfer and mixing is required.

According to the state of art, an infusion solution and dry or liquid form drugs are admixed by a syringe and by removal from and addition to different containers, before a mixed infusion solution is ready for infusion. Contaminations cannot be eliminated due to pressure differentials between the different containers and the atmosphere, and due to the free handling of the syringe. Such a practice requires working under a suction apparatus which is considerably disturbing in medical work.

Furthermore, injection ports on infusion containers have been proposed which improve the mixing of the agents mentioned but do not eliminate the problem of contamination. A further improvement of the same object is known from the EP 0 363 770 A1 which discloses a connector for pharmaceutic solutions, and from EP 0 330 130 which disclose a container for infusion solutions. The connector described in the EP 0 363 770 substantially consists of a tubular coupling portion and a shutoff device for closing the former. The coupling portion is comprised of a hollow insertion pin and a hollow portion attached thereto which permits insertion into a hose-like connector of a container. The hollow portion is closed by a stop-cock detachable from the outside. However, even when employing containers having rubber stopper seals, elimination emission of aerosols is not assured.

Furthermore, connectors are known from the U.S. Pat. No. 4,675,020 and from the EP 0 028 198 which do not solve the problem of contamination as desired and, additionally, similar to the above disclosed device, only permit the connection of two containers filled with pharmaceutic solutions. Thus, such devices are only applicable when, for example, the dissolving of an agent requires two solvents.

SUMMARY OF THE INVENTION

It is an object of the invention to provide a connector for joining drug (cytostatica) containers to an administration system which eliminates contamination of the environment around the drug container from the connecting state up to the removal of residuals and which does so without considerable expenditures for the connector apparatus.

The present invention provides a connector which is particularly applicable in ambulant treatment and which, when used, does not put high requirements upon medical care workers and releases the latter from any contamination problems.

Briefly stated, the present invention provides a one-piece dispensing device for the contamination-free administration of medicaments is particularly suitable for use in ambulant treatment. The invention provides a connector for connecting medicament containers to instruments by which the medicaments are administered. The connector is designed to prevent, without a complex apparatus, contamination of the surroundings during connection of the container and until its disposal. The dispensing device has at least one coupling member to create a non-releasable connection with a medicaments container. The coupling member has an insertion pin and barbed surfaces to accommodate the medicaments container. The coupling member is non-releasably connected via a tube to a flexible container which is to be filled with gas. The flexible container is non-releasably connected to a further tube outlet and a mechanically actuated stop valve is incorporated in each of the connecting tubes.

In accordance with these and other objects of the invention, there is provided a one piece dispensing device for contamination-free administration of drugs (cytostatica) comprising at least one coupling member for establishing a non-detachable connection with a drug containing container, the coupling member including an insertion pin and a barbed area for receiving the drug container, the coupling member being non-detachably connected via a hose connection to a receptacle permitting filling with a gas prior to a first application of the device, the receptacle being non-detachably connected to a further hose-like outlet, in each of the connection lines a respective mechanically operable stop valve being installed.

According to a feature of the invention, the coupling member is constituted of a cup-shaped inelastic hollow body enclosing and sealing the insertion pin, and being provided with an interior reception profile ensuring a non-detachable contact to a drug container, wherein the height of the tip of the insertion pin relative to a the barbed area of the reception profile is adapted to actuate an arresting effect of the barbed area with the drug container after piercing an insertion base of the latter.

According to a further embodiment of the present invention the is provided a dispensing device for contamination-free administration of a drug provided in a drug container with a seal, the dispensing device comprising: at least one coupling member for establishing a non-detachable connection with the drug container, the coupling member including an insertion pin for penetrating the seal of the drug container and a coupling mechanism for non-detachably engaging the drug container to establish the non-detachable connection; a flexible container fillable with a gas; a first conduit having a first stop valve which is openable and closeable, the first conduit connecting the coupling member with the flexible container to permit passage of the drug between the flexible container and the drug container; a second conduit having a second stop valve which is openable and closeable, the second conduit communicating with the flexible container for operation as an outlet.

BRIEF DESCRIPTION OF THE DRAWINGS

The invention will be explained in more detail by reference to the following figures wherein.

DETAILED DESCRIPTION OF THE INVENTION

Figure 1:
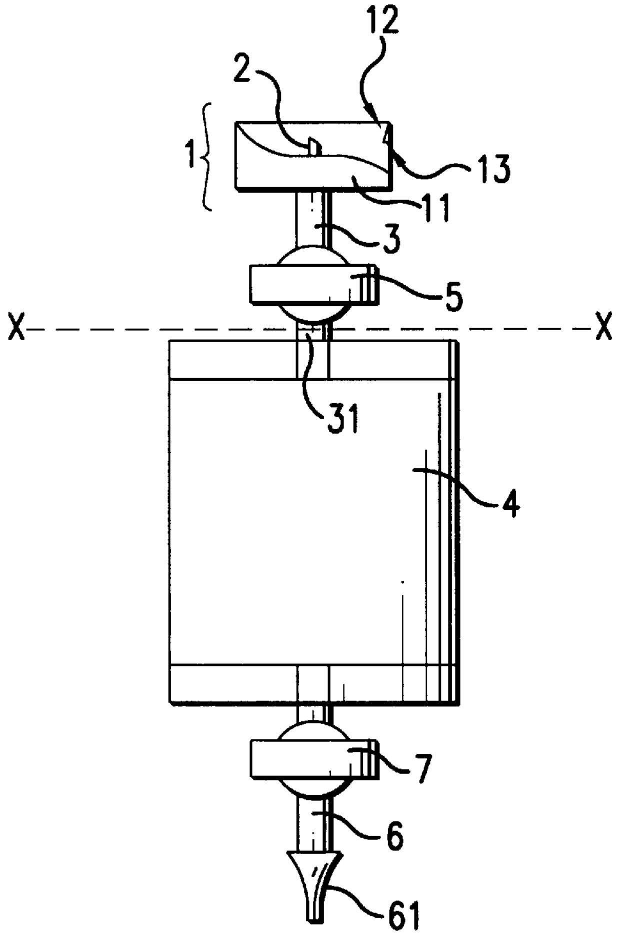
FIG. 1 shows an embodiment of the present invention for administering drugs (cytostatica) in liquid form.

Referring to FIG. 1, a connector is shown comprising a coupling member 1 which includes an insertion pin 2. The coupling member 1 is non-detachably connected by adhesives or by welding to a flexible container 4 via hose connections 3 and 31. The flexible container 4 is provided to accept filling with a gas. A mechanically operable stop valve 5 interconnects hose connections 3 and 31. The flexible container 4 also is preferably non-detachably provided with a hose-like outlet 6 and a further mechanical stop valve 7 integral with the outlet 6. The outlet 6 provides for making hose connection (not shown) to patients, such as with conventional catheters. The coupling member 1 consists of a cup-shaped inelastic hollow body 11 which has a contoured interior surface 12. The hollow body 11 is preferably and additionally coated with an elastic sealing means (not shown). The contoured interior surface 12 tapers inward and carries at least one barb member 13.

Figure 3A:
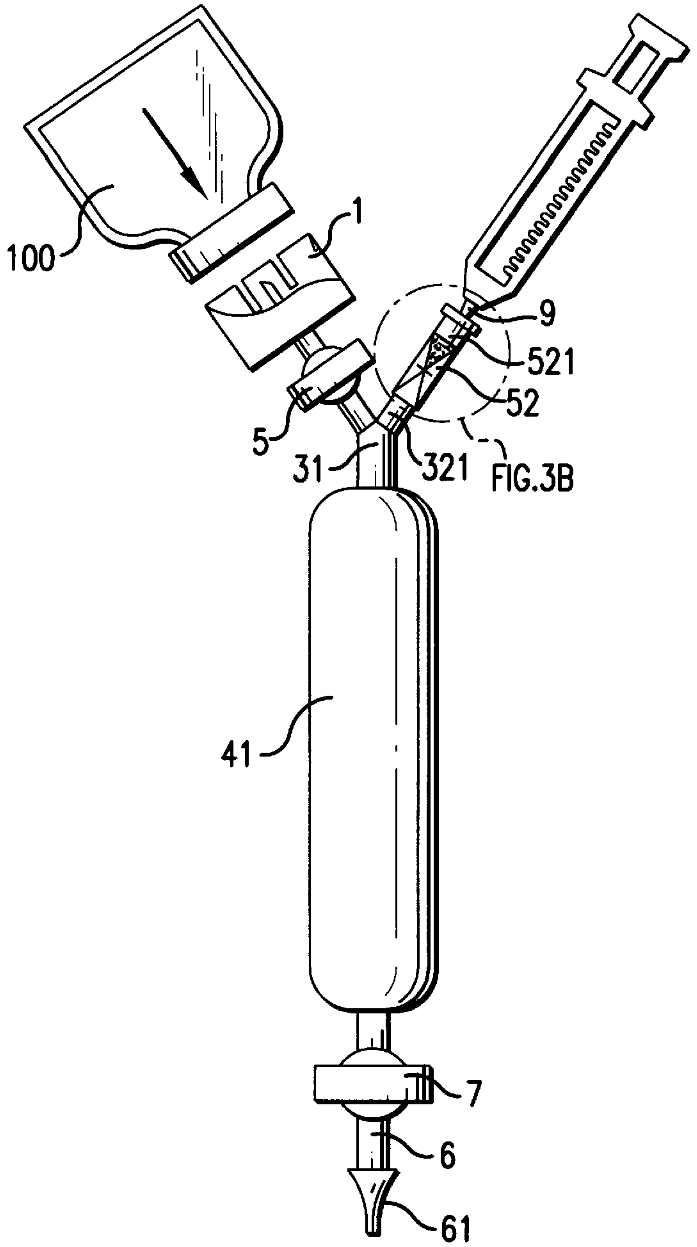
FIG. 3 shows an embodiment of the present invention for dissolving drugs sold in solid form, in which a supply means for variable amounts of solvents is provided.
Figure 3B:
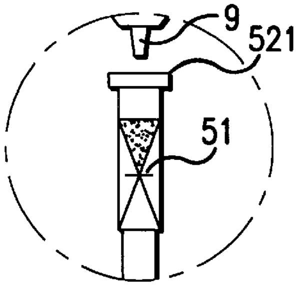

Referring to FIG. 3, in order to administer a drug (cytostatica) available in containers having a neck of which permits insertion into the coupling member 1, a drug container 100 is inserted into the coupling member 1 and pressed on the latter. Typically the height of the penetration depth of the insertion pin 2 relative to the barbed member 13 is so defined that, when the insertion pin 2 has pierced an insertion base of the drug container 100, the barbed members 13 catch corresponding engagement areas of the neck of the drug container 100 and thus non-detachably connect the latter to the coupling member 1. Thus it is ensured that during connection and infusion subsequently carried out, neither the health care workers nor the environment is contaminated by aerosols or the like emitted from the drug container 100.

Referring again to FIG. 1, subsequent to establishment of connection of the drug container 100, a path is opened via the mechanically operable stop valve 5 to a sterile flexible container 4 which is, for example, filled with air. It is feasible to press the air into the drug container 100 and subsequently withdraw a required dosage of the liquid drug from the container 100 into the flexible container 4. Only then is the path via the outlet 6 for the drug to be administered to the patient opened by means of the stop valve 7. Conduction means attached to the outlet 6, conventionally connected to an adapter plug nozzle 61 of the outlet 6, are not represented in more detail.

Figure 2:
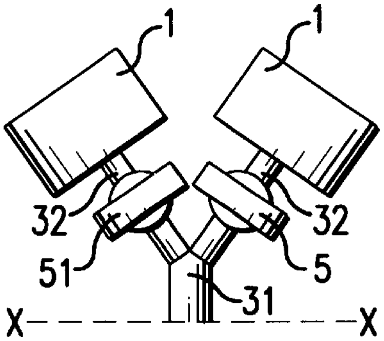
FIG. 2 shows an embodiment of the present invention for dissolving drugs sold in solid form (cytostatica) and for mixing two liquid drugs.

Referring to FIG. 2, a further embodiment of the present invention is shown which differs from the embodiment of FIG. 1 by a different embodiment above a line X—X at the hose-connection 31. Typically, two hose connections 32 branch off from the hose connection 31, non-detachably connected to the latter. One hose connection 31 includes the mechanically operable stop valve 5 and the other hose connection includes mechanically operable stop valve 51. In a preferable embodiment, both of the hose-connections 32 are each provided with the coupling member 1 in analogy to FIG. 1.

The embodiment of FIG. 2 is particularly suitable for administering drugs (cytostatica) on sale in dry form, such as powder. The procedure is as follows First the first coupling member 1 is connected to a container with an appropriate solvent inside and, subsequently, the second coupling member 1 is connected with a container containing the drug to be passed into solution. After opening the stop valve 51 an appropriate volume of the solvent passes into the flexible container 4, the stop valves 7 and 5 being in the OFF-state. Then the stop valve 51 is closed and the stop valve 5 opened to open the path to the container with the drug (cytostatica) and pass the solvent into solution with the drug as the flexible container 4 is kept under pressure. Subsequent to the above solution process, the dissolved drug is permitted to return to the flexible container 4. The valves 5 and 51 are set to the OFF-state and the dissolved drug can be administered as described in analogy to FIG. 1.

It is obvious also to employ the embodiment shown in FIG. 2 for dosed mixing of two liquid drugs the containers of which are connectable to the first and the second coupling members 1.

Referring again to FIG. 3, a particularly advantageous administering device of the present invention, discussed above with regard to the coupling member 1 and the insertion pin 2 connecting with the container 100, has the coupling member 1 non-detachably connected by adhesives or welding to a flexible gas-filled self-supporting container 41 via a hose-connection 31. The mechanically operable stop valve 5 is provided within the hose-connection 31. Furthermore, in analogy to FIG. 1, the flexible container 41 is, preferably non-detachably, provided with the hose-like outlet 6 integrated with the mechanical stop valve 7.

In a further particularly advantageous embodiment of the present invention, a second hose-connection 321 branches off the first hose-connection 31, also non-detachably connected with one another. A check valve 52 is provided in the second hose-connection 321 operating as a mechanical stop valve with the locking effect in opposite direction to the flexible container 41. The check valve 52 is provided with a socket 521 adapted for receiving a cone-shaped connection piece 9. The socket 521 preferably is embodied as a Luer-lock joint which, in particular, is adapted for receiving a tapering end portion of a conventional syringe. Furthermore, it is feasible to insert an analogous stop valve 5 between the check valve 52 and the hose connection 321.

According to the invention, the Luer-lock joint is preferably embodied in such a manner that the same when inserted into the check valve 52 opens the latter via the nozzle end-portion 9 of the syringe when the connection is effected. The proposed solution is particularly suited for administration of drugs (cytostatica) which are at one's disposal in dry form, such as powder. The procedure is as follows:

First the container 100 which contains the drug to be dissolved is connected by exerting pressure in a direction indicated by the arrow; the path to the hose connection 31 being still closed by the stop valve 5. Then a syringe which is conventionally and variably filled with a sodium chloride solution, depending on the dosage of the dry form drug to be dissolved, is inserted via its nozzle end portion 9 into the Luer-lock joint 521 to effect contact with the same and to open the check valve 52. The solvent is now permitted to enter the flexible and self-supporting gas-, preferably, air-filled container 41. Subsequently, the syringe is removed and the check valve 52 ensures a contamination-free seal preventing contamination of the surrounding environment.

Alternatively, when it is required that the syringe or any other replacement container for the solvent remain in the connected state, a further stop valve is provided between the check valve 52 and the hose connection 31. The further stop valve must be closed after the solvent has been filled in the flexible container 41.

The first stop valve 5 to the coupling member 1 is then opened and an appropriate dosage of the solvent is pressed into the container 100 with the drug to be dissolved and, after dissolution, the solution is transferred into the flexible container 41. the first stop valve 5 is then closed and the drug container 100 remains in an airtight and non-detachable connection with the coupling member 1. The release of the dissolved drug to the patient is obtained by opening the stop valve 7.

It lies within the scope of the invention to embody the stop valve 5 as a three-way valve installed adjacent the flexible container 41 in the hose connection 31.

In contrast to the embodiment according to FIG. 2 where the solvent for mixing solutions has to be at one's disposal in doses as on sale and in prepared containers, what might, in particular, involve difficulties in small medical practices due to the fact that, for example, sodium chloride solutions as rule are only available in large fillings, the embodiment according to FIG. 3 has the advantage that, due to the second connection port, a contamination-free coupling of a conventional syringe with variable dosage is feasible. Furthermore, the range of drug doses to be dissolved is extended at will.

Figure 4:
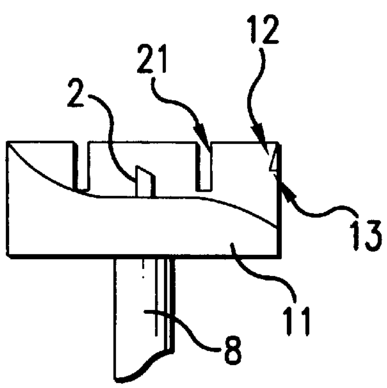
FIG. 4 shows a detailed representation of an embodiment of a one-piece coupling according to the present invention.

Referring to FIG. 4, a partially sectional view of an embodiment of the coupling member 1 is shown in detail. All elements designated, namely, the insertion pin 1, hollow body 11, contoured interior surface 12, and a connection piece 8, which preferably are made of plastics, according to the present invention are embodied as one piece, that is, the insertion pin 2 is also an integral part of the coupling member 1. Preferably, it is feasible to manufacture the entire coupling member 1 as a one-piece injection-moulded member. Notches 21 are also generated with the plastics injection moulding of the coupling member 1 and are adapted to receive corresponding counterparts on the drug container.

The present invention is not restricted to the number of connections disclosed. It, however, is essential that a flexible container 4, 41 permitting gas filling is employed which is provided with at least two connection lines to permit a selective opening and closing to a definitely embodied coupling means and in direction of the drug delivery, respectively. Typically, the entire administration system, including an already gas-filled (preferably air) flexible container is made available in sterile form. Alternatively, it is feasible to fill the flexible container with a gas only prior to application.

We claim:

1. A dispensing device for contamination-free administration of a drug provided in a drug container with a seal, the dispensing device comprising:

at least one coupling member for establishing a non-detachable connection with the drug container, said coupling member including an insertion pin for penetrating the seal of the drug container and at least one barb member for engaging the drug container to establish said non-detachable connection;

a flexible container fillable with a gas;

a first conduit having a first stop valve which is openable and closeable, said first conduit connecting said coupling member with said flexible container to permit passage of the drug between said flexible container and the drug container; and a second conduit having a second stop valve which is openable and closeable, said second conduit communicating with said flexible container for operation as an outlet.

2. The dispensing device as claimed in claim 1 further comprising a third conduit having a third stop valve which is openable and closeable, said third conduit communicating with said flexible container to permit passage of matter into said flexible container wherein at least said first conduit has said coupling member.

3. The dispensing device as claimed in claim 1 or 2, wherein said coupling member includes a cup-shaped hollow body encircling and sealing around said insertion pin, and said cup-shaped hollow body has a contoured inner surface with said barb member disposed thereon at a position relative to a tip of said insertion pin such that the barb member non-detachably engages the drug container after piercing of the seal of the drug container by said insertion pin.

4. The dispensing device as claimed claim 3, wherein said coupling member includes said hollow body, said contoured inner surface, and said insertion pin, and is manufactured integrally as one piece.

5. The dispensing device as claimed in claim 1, wherein said flexible container is a self-supporting gas-filled flexible container.

6. The dispensing device as claimed in claim 1 or 5, further comprising a third conduit having a check valve, said third conduit communicating with said flexible container to permit passage of matter into said flexible container, said check valve having a socket for receiving a nozzle to permit supply of variable amounts of solvents into said flexible container.

7. The dispensing device according to claim 6, wherein said socket is a Luer-lock joint which opens the check valve.

8. A dispensing device for contamination-free administration of a drug provided in a drug container with a seal, the dispensing device comprising:

at least one coupling member for establishing a non-detachable connection with the drug container, said coupling member including an insertion pin for penetrating the seal of the drug container and a coupling mechanism for non-detachably engaging the drug container to establish said non-detachable connection;

a flexible container fellable with a gas;

a first conduit having a first stop valve which is openable and closeable, said first conduit connecting said coupling member with said flexible container to permit passage of the drug between said flexible container and the drug container;

a second conduit having a second stop valve which is openable and closeable, said second conduit communicating with said flexible container for operation as an outlet.

9. The dispensing device as claimed in claim 8 further comprising a third conduit having a third stop valve which is openable and closeable, said third conduit communicating with said flexible container to permit passage of matter into said flexible container.

10. The dispensing device as claimed in claim 8, wherein said coupling member includes a cup-shaped hollow body encircling and sealing around said insertion pin, said cup-shaped hollow body having a contoured inner surface, and said coupling mechanism includes a barb member disposed on said contoured inner surface at a position relative to a tip of said insertion pin such that the barb member non-detachably engages the drug container after piercing of the seal of the drug container by said insertion pin.

11. A dispensing device for contamination-free administration of a drug provided in a drug container with a seal, the dispensing device comprising:

at least one coupling member for establishing a non-detachable connection with the drug container, said coupling member including an insertion pin for penetrating the seal of the drug container and a coupling mechanism for non-detachably engaging the drug container to establish said non-detachable connection;

a flexible container fillable with a gas;

a first conduit having a first stop valve which is openable and closeable, said first conduit connecting said coupling member with said flexible container to permit passage of the drug between said flexible container and the drug container;

a second conduit having a second stop valve which is openable and closeable, said second conduit communicating with said flexible container for operation as an outlet; and a third conduit having a check valve, said third conduit communicating with said flexible container to permit passage of matter into said flexible container, said check valve having a socket for receiving a nozzle to permit supply of variable amounts of solvents into said flexible container.

12. The dispensing device according to claim 11, wherein said socket is a Luer-lock joint which opens the check valve.

* * * * *